(12) United States Patent
Tanielian et al.

(10) Patent No.: US 10,585,070 B2
(45) Date of Patent: Mar. 10, 2020

(54) TAMPER-SENSITIVE RESONATOR AND SENSOR FOR DETECTING COMPARTMENT OPENINGS

(71) Applicant: The Boeing Company, Chicago, IL (US)

(72) Inventors: Minas H. Tanielian, Bellevue, WA (US); Dan J. Clingman, Milton, WA (US)

(73) Assignee: THE BOEING COMPANY, Chicago, IL (US)

( * ) Notice: Subject to any disclaimer, the term of this patent is extended or adjusted under 35 U.S.C. 154(b) by 232 days.

(21) Appl. No.: 15/660,051

(22) Filed: Jul. 26, 2017

(65) Prior Publication Data
US 2019/0033262 A1   Jan. 31, 2019

(51) Int. Cl.
*B64D 11/06* (2006.01)
*G01N 29/12* (2006.01)
*B64D 11/00* (2006.01)

(52) U.S. Cl.
CPC ......... *G01N 29/12* (2013.01); *B64D 11/0631* (2014.12); *B64D 11/00* (2013.01); *G01N 2291/014* (2013.01); *G01N 2291/2694* (2013.01)

(58) Field of Classification Search
CPC ........... G01N 29/12; G01N 2291/2694; G01N 2291/014; B64D 11/00
USPC ........................................................ 73/579
See application file for complete search history.

(56) References Cited

U.S. PATENT DOCUMENTS

| | | | | |
|---|---|---|---|---|
| 2,791,328 A | * | 5/1957 | Beardsley | G01R 31/18 209/560 |
| 9,070,068 B2 | * | 6/2015 | Coveley | G06K 19/07749 |
| 2006/0214789 A1 | * | 9/2006 | Posamentier | G06K 19/0716 340/545.6 |
| 2010/0156606 A1 | * | 6/2010 | Gold | H04Q 9/00 340/10.4 |
| 2016/0099401 A1 | * | 4/2016 | Matsugi | H03H 9/02102 310/321 |
| 2016/0275769 A1 | * | 9/2016 | McIntosh | G08B 13/2414 |

FOREIGN PATENT DOCUMENTS

CN       2037208540      *  7/2014

\* cited by examiner

*Primary Examiner* — Jacques M Saint Surin
(74) *Attorney, Agent, or Firm* — MH2 Technology Law Group LLP (57) ABSTRACT

According to various embodiments, a system for, and method of, detecting the opening of a lid of a compartment constructed of a rigid material. The system includes a resonator disposed on a wall of the compartment, where the resonator has a resonant frequency of mechanical vibration. The system also includes a member disposed on the lid of the compartment and positioned to perturb the resonator upon opening the lid, such that opening the lid causes the resonator to mechanically vibrate at the resonant frequency. The system also includes an electronic sensor disposed on the compartment to detect vibrations at the resonant frequency. The system also includes an interface communicatively coupled to the electronic sensor and configured to provide a signal indicating lid opening data representing at least one opening of the lid.

20 Claims, 7 Drawing Sheets

TAMPER-SENSITIVE RESONATOR AND SENSOR FOR DETECTING COMPARTMENT OPENINGS

FIELD

This disclosure relates generally to security of compartments, e.g., aircraft compartments.

BACKGROUND

Aircraft typically have many compartments of various types. Such compartments may be accessible from the inside or from the outside of the aircraft. For example, some commercial aircraft have compartments for life vests that are accessible from inside the aircraft. In some cases, e.g., for security purposes, it is desirable to know whether an aircraft compartment has been opened.

SUMMARY

According to various embodiments, a system for detecting opening of a lid of a compartment constructed of a rigid material is disclosed. The system includes a resonator disposed on a wall of the compartment, where the resonator has a resonant frequency of mechanical vibration; a member disposed on the lid of the compartment and positioned to perturb the resonator upon opening the lid, such that opening the lid causes the resonator to mechanically vibrate at the resonant frequency; an electronic sensor disposed on the compartment to detect vibrations at the resonant frequency; and an interface communicatively coupled to the electronic sensor and configured to provide a signal indicating lid opening data representing at least one opening of the lid.

Various optional features of the above embodiments include the following. The compartment may be an aircraft compartment. The resonator may be positioned on an inside wall of the compartment. The sensor may be positioned outside of the compartment. The interface may include a radio frequency transmitter configured to send a radio frequency signal indicating an opening of the lid. The system may include a base station configured to receive the radio frequency signal. The radio frequency transmitter may include a Radio Frequency Identification (RFID) tag. The RFID tag may further include an electronic memory configured to store an indication of a number of openings of the lid. The system may further include an electronically stored database including expectation data representing at least one of an intended number of openings of the lid or an intended frequency of openings of the lid; and at least one electronic processor configured to provide an alert upon determining that the lid opening data is inconsistent with the expectation data. The resonant frequency of the resonator may be user adjustable.

According to various embodiments, a method of detecting an opening of a lid of a compartment constructed of a rigid material is disclosed. The method includes receiving mechanical vibrations at an electronic sensor positioned on a wall of the compartment, where a resonator having a resonant frequency of mechanical vibration is positioned on the compartment, and where a member disposed on the lid is positioned to perturb the resonator upon opening the lid, such that opening the lid causes the resonator to mechanically vibrate at a resonant frequency; obtaining an electrical signal from the sensor representing the mechanical vibrations; processing the electrical signal to produce lid opening data indicating at least one opening of the lid; and providing the lid opening data through an interface.

Various optional features of the above embodiments include the following. The compartment may be an aircraft compartment. The resonator may be positioned on an inside wall of the compartment. The electronic sensor may be positioned on an outside wall of the compartment. The providing the lid opening data through the interface may include sending a radio frequency signal. The method may include positioning a base station to receive the radio frequency signal. The sending the radio frequency signal may include sending the radio frequency signal in response to an excitation of a Radio Frequency Identification (RFID) tag. The radio frequency signal may provide an indication of a number of openings of the lid. The method may include establishing an electronically stored database including expectation data representing at least one of an intended number of openings of the lid or an intended frequency of openings of the lid; and providing an alert upon determining that the lid opening data is inconsistent with the expectation data. The resonant frequency of the resonator may be adjustable.

BRIEF DESCRIPTION OF THE DRAWINGS

Various features of the examples can be more fully appreciated, as the examples become better understood with reference to the following detailed description, when considered in connection with the accompanying figures, in which.

DESCRIPTION

Reference will now be made in detail to the disclosed examples, which are illustrated in the accompanying drawings. Wherever possible, the same reference numbers will be used throughout the drawings to refer to the same or like parts. In the following description, reference is made to the accompanying drawings that form a part thereof, and in which is shown by way of illustration specific examples. These examples are described in sufficient detail to enable those skilled in the art to practice them and it is to be understood that other examples may be utilized and that changes may be made without departing from the scope of the disclosure. The following description is, therefore, merely exemplary.

It is sometimes desirable to know if a compartment of an aircraft has been opened, and if so, how many times over a given period. Some solutions utilize a sensor in the compartment coupled to a passive Radio Frequency Identification ("RFID") tag that communicates with an external computer system. These types of solutions are acceptable when the RFID tag can communicate through a dielectric compartment wall. Metal enclosed compartments, however, can effectively form a Faraday cage, through which radio frequencies cannot effectively penetrate. Therefore, solutions that rely on RFID tags inside compartments are not suitable for metal compartments.

Some embodiments can detect the opening of a metallic compartment using a sensor placed away from the opening itself, e.g., on an outside, rear surface of the compartment, so that the person who is opening the compartment has neither direct access to the sensor nor visibility to it and thus may not even be aware of its existence. Some embodiments utilize a mechanical resonator attached to the compartment and a member attached to the lid, such that opening the lid moves the member to perturb the resonator, causing it to mechanically vibrate with a characteristic resonant frequency. In some embodiments, the mechanical vibration of the resonator can only be activated by the opening action itself. In some embodiments, the resonator is firmly attached to the wall of the metal enclosure, which is much larger and more massive than the resonator itself, so that external vibrations that couple to the enclosure's natural vibration modes do not couple to the natural resonant frequency of the resonator. The resonator may be implemented as a steel cantilever beam, sufficiently small and stiff to have a resonant frequency high enough to achieve this effect. A sensor, such as a piezoelectric bimorph, picks up the vibration of the resonator and generates a voltage indicative of the resonator's characteristic resonant frequency. The piezoelectric bimorph may have sufficient current to power a counter in an electronic persistent memory that indicates a number of openings. The counter may be implemented in a memory section of an RFID chip that can communicate the opening information when an RFID tag present on the RFID chip is interrogated by a reader. According to some embodiments, this communication is conducted in a "pull" fashion, when the associated system needs the information. Some embodiments include a battery (e.g., the type used for battery-assisted, passive RFID chips) that supplies current to the RFID chip. The RFID chip can perform signal processing operations on the data from the piezoelectric bimorph to generate accurate opening count data. Some embodiments use a bandpass filter tuned to the resonant frequency of the resonator as part of the signal processing.

Figure 1:
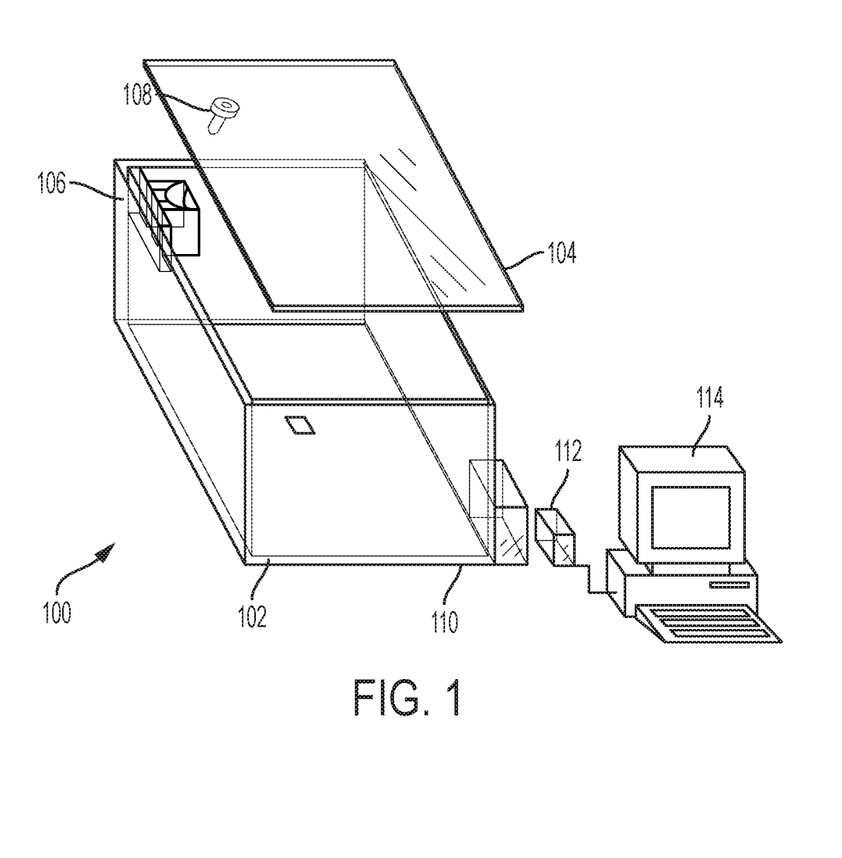
FIG. 1 is a schematic diagram of a system according to some embodiments.

FIG. 1 is a schematic diagram of a system 100 according to some embodiments. All or part of system 100 may implement all or part of methods 500 and 600 as shown and described in reference to FIGS. 5 and 6, respectively, below. System 100 includes compartment 102 equipped with lid 104. Though depicted as fully detachable in FIG. 1, in some embodiments, lid 104 may be handedly attached, for example, to compartment 102. Compartment 102 and lid 104 may be constructed from a rigid, conductive material, e.g., metal, metal composite, or metal laminate.

Bracket 106 is attached to, or integrated with, compartment 102. Bracket 106 includes a small resonant element, or "resonator", which may be implemented as a cantilever beam present on bracket 106 (shown and described further below in reference to FIG. 2). In embodiments in which bracket 106 is attached to compartment 102, it may be attached thereto using epoxy resin, for example. Bracket 106 (and its resonator) may be positioned inside of compartment 102, as shown, or outside of compartment 102. According to some embodiments, bracket 106 (and its resonator) is positioned inside, or outside, of lid 104. Bracket 106 is further shown and described in reference to FIGS. 2 and 3, below.

Member 108 is attached to lid 104 and positioned in such a way that it momentarily interfaces with the resonator of bracket 106 when lid 104 is opened, perturbing the resonator in a manner that causes it to mechanically vibrate at its resonant frequency. Member 108 is further shown and described in reference to FIG. 3, below.

System 100 further includes sensor module 110. Sensor module 110 is attached to compartment 102, typically in a place that is invisible and/or inaccessible to a person capable of opening compartment 102. Thus, sensor module 110 may be placed on an outside wall of compartment 102, e.g., away from a position of bracket 106. Sensor module 110 detects vibrations of compartment 102 at the resonant frequency of the resonator of bracket 106 and produces a corresponding electrical signal. Sensor module processes the electrical signal to generate and store lid opening data representing a number of openings of compartment 102. Sensor module 110 may transmit a signal representing the lid opening data to reader device 112. The transmission may be by way of reader device 112 interrogating a persistent memory of an RFID chip aboard sensor module 110. Sensor module 110 is further shown and described in reference to FIG. 4, below.

Reader device 112 may be a standard RFID reader, configured to communicatively couple with an RFID tag aboard an RFID chip of sensor module 110. Reader device 112 may be communicatively coupled, e.g., by way of a cable, to computing device 114.

Computing device 114 may be a stand-alone computer, or a computer module that forms part of a larger system. Computing device 114 may obtain a signal representing the lid opening data from reader device 112 and further process or act on such data. For example, computing device 114 may compare the lid opening data to expected lid opening data, and alert a person if the two are inconsistent. Computing device 114 may implement all or part of methods 500 and 600, as shown and described in reference to FIGS. 5 and 6, respectively, below.

Figure 2:
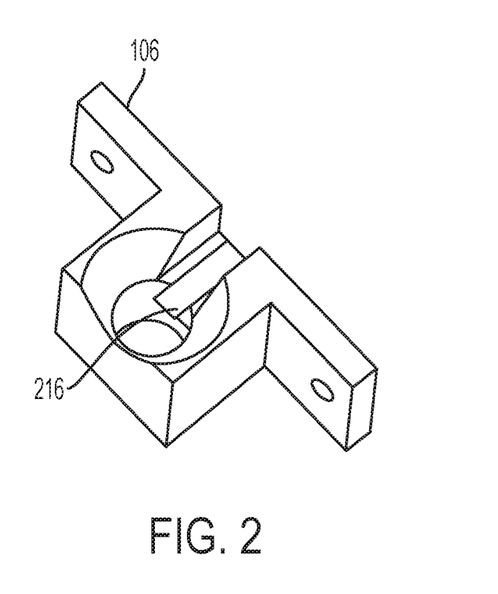
FIG. 2 is a perspective view of a bracket with a resonator according to some embodiments.

FIG. 2 is a perspective view of bracket 106 with resonator 216, according to some embodiments. Bracket 106 may be constructed of metal, e.g., steel or other alloy. Bracket 106 may include mounting holes placed to permit attachment of bracket 106 to compartment 102 by way of bolts or rivets, for example. Bracket 106 may further, or alternately, have a surface amenable to attachment to compartment 102 using adhesive, e.g., epoxy resin. Bracket 106 includes resonator 216, implemented by way of non-limiting example as a cantilever beam. Note that resonator 216 protrudes slightly into the hole through bracket 106 as shown in FIG. 2.

Resonator 216 may be configured to have a resonant frequency in the low kilohertz range, e.g., between 1 and 500 kHz. The configuration may utilize Mersenne's Law, noting that resonant frequency is inversely proportional to the length of the cantilever beam.

According to some embodiments, the resonant frequency of resonator 216 is adjustable, e.g., by moving a sliding weight to a different position along the cantilever. According to some embodiments, the resonant frequently is adjustable, e.g., by removing material from the end of the cantilever beam to adjust its length. Such material may be removed using a metal file, for example. Other techniques for adjusting the resonant frequency of resonator 216 are possible.

Figure 3:
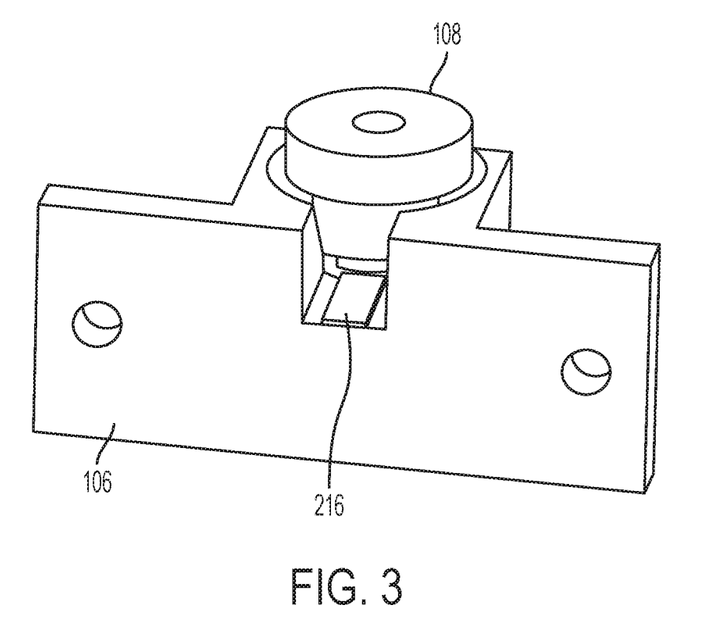
FIG. 3 is a perspective view of the bracket of FIG. 2 engaging a perturbing member according to some embodiments.

FIG. 3 is a perspective view of bracket 106 engaging member 318 according to some embodiments. As shown, member 318 momentarily engages resonator 216 in such a way that, as member 318 enters or exits the hole formed in bracket 106, it perturbs resonator 216, causing it to mechanically vibrate at its resonant frequency. Member 318 may be constructed from any durable material, e.g., metal or hard plastic.

Figure 4:
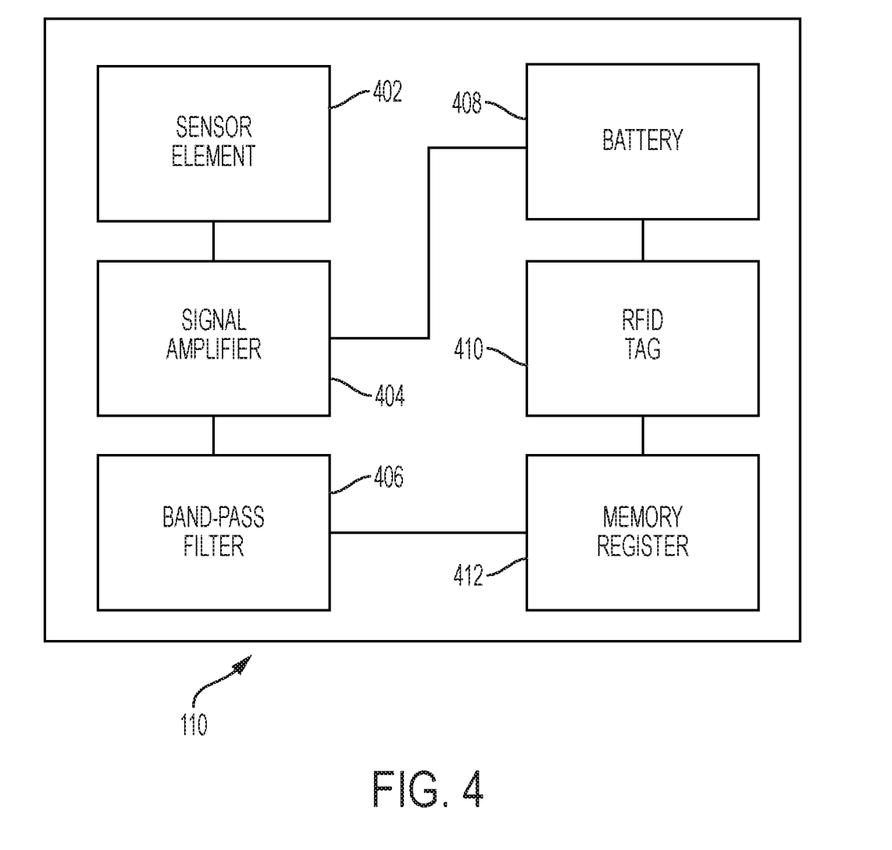
FIG. 4 is a schematic diagram of a sensor module according to some embodiments.

FIG. 4 is a schematic diagram of sensor module 110 according to some embodiments. According to some embodiment, sensor module 110 may be integrated into a unitary form factor, e.g., a plastic and/or metal box. Sensor module 110 may include one or more signal acquisition and signal processing elements, any of which, or any combination of which, may be implemented on board an RFID integrated circuit. Thus, sensor module 110 includes sensor element 402, which detects mechanical vibration and generates a corresponding electrical signal. Sensor element 402 may be implemented as a piezoelectric bimorph, for example. Sensor element 402 may be physically disposed on the outside of, or physically coupled to the outside surface of, sensor module 110, such that it may easily receive mechanical vibrations produced by resonator 216. Sensor element 402 is electrically coupled to one or more signal processing elements that convert appropriate signals into indications of lid openings, that is, lid opening data. Thus, sensor element 402 may be coupled to signal amplifier 404, which draws power from battery 408. Signal amplifier 404 may output to band-pass filter 406, which may be implemented as a relatively high-Q filter tuned to the resonant frequency of resonator 216. Band-pass filter 406 may be tunable, e.g., for embodiments in which the resonant frequency of resonator 216 is itself adjustable. Band-pass filter 406 may output to memory register 412. Memory register 412 may include persistent memory, volatile memory, and/or computer logic sufficient to convert outputs of one or more of sensor element 402, signal amplifier 404, or band-pass filter 406 to lid opening data representing a number of openings of lid 104 of compartment 102 over a known time period or prior to a known event occurrence. The lid opening data may be stored in persistent and/or volatile memory of memory register 412. The storage location may be accessible to RFID tag 410, which may transmit the lid opening data to reader device 112 using, e.g., any known RFID protocol. RFID tag 410 may draw power from battery 408, which may be implemented as a battery amenable to boosting passive RFID tags. Thus, RFID tag 410 is an interface to sensor module 110.

Computer logic implemented in memory register 412 may account for various physical phenomena in correctly determining that an opening event has occurred and excluding false positives. For example, the computer logic may only count a detection of the resonant frequency of resonator 216 as an opening event if the duration of the detection exceeds some predetermined threshold. This may account for member 318 snubbing out vibrations of resonator 216 upon lid 104 closing on compartment 102, but permitting such vibrations to persist upon lid 104 opening from compartment 102, for example. Other processing is possible.

Figure 5:
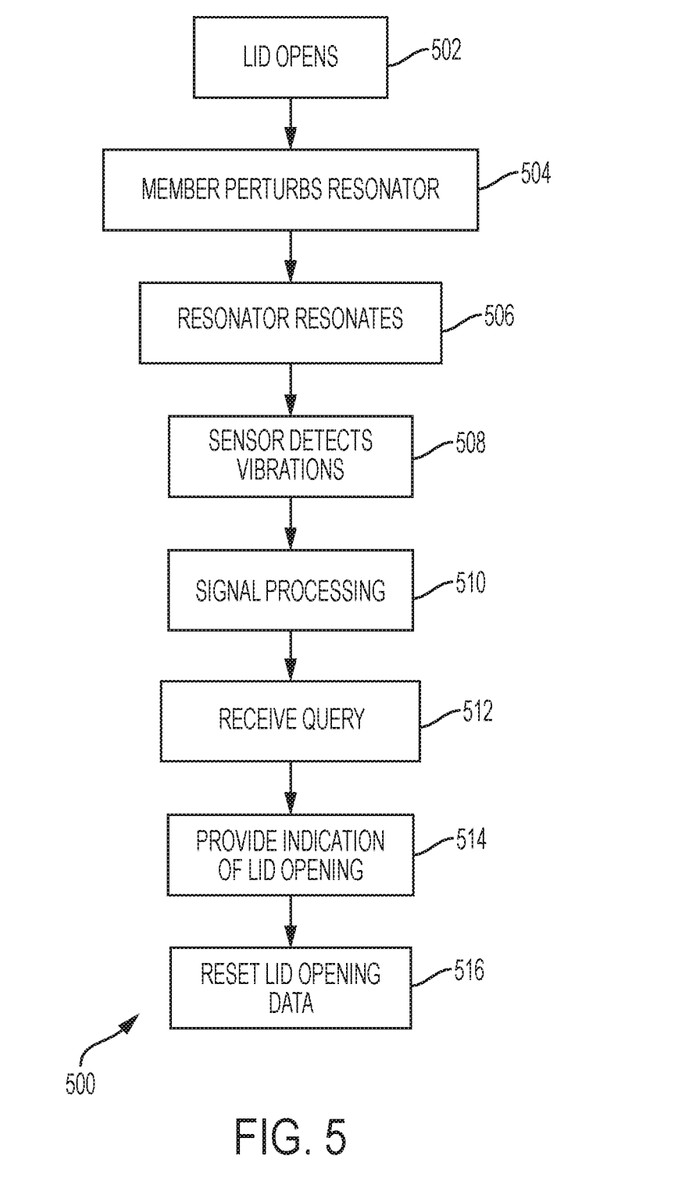
FIG. 5 is a flow diagram of a method of detecting an opening of a compartment lid according to some embodiments.

FIG. 5 is a flow diagram of a method 500 of detecting an opening of a compartment lid according to some embodiments. Method 500 may be implemented in whole or in part by all or part of system 100 of FIG. 1, for example.

At block 502, lid 104 is opened from compartment 102, e.g., by a human such as an airline employee or a malevolent individual. The opening of lid 104 causes member 108 to perturb resonator 216 at block 504, causing it to vibrate at its resonant frequency at block 506.

At block 508, sensor element 402 detects the mechanical vibrations of resonator 216. Sensor element 402 passes the corresponding representative electrical signal to circuitry in sensor module 110, and at block 510 sensor module 110 processes the electrical signal as shown and described above in reference to FIG. 4. According to some embodiments, the result of block 510 is that sensor module 110 stores in internal persistent memory lid opening data, representing a number of lid openings since a prior reading of the lid opening data.

At block 512, sensor module 110 provides lid opening data, e.g., to reader device 112. There are a number of ways that sensor module 110 may provide the lid opening data. For example, reader device 112 may read RFID tag 410 using a known RFID protocol to retrieve a tally of openings of lid 104. The RFID tag reading may cause the persistent and/or volatile memory that holds the tally to reset to zero. In this manner, the number of lid openings indicated by the lid opening data read by reader device 112 represents a total number of openings since the last RFID reading by reader device 112.

Figure 6:
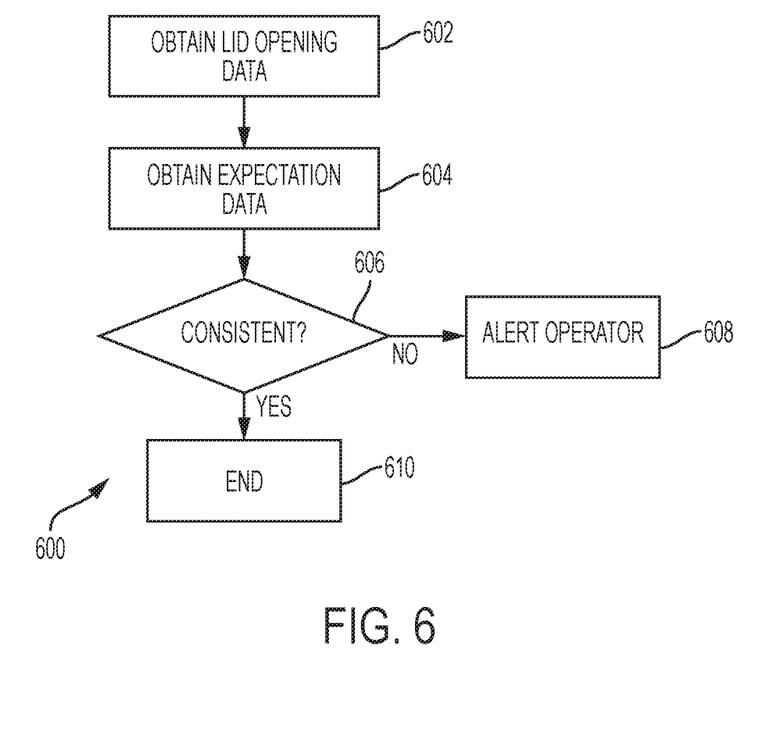
FIG. 6 is a flow diagram of a method of reporting at least one noncompliant lid opening according to some embodiments.

FIG. 6 is a flow diagram of a method 600 of reporting at least one noncompliant lid opening according to some embodiments. Method 600 may be implemented in whole or in part by all or part of system 100 of FIG. 1, for example.

At block 602, method 600 obtains lid opening data representing at least one opening of lid 104. According to some embodiments, the lid opening data represents a total number of lid openings since the last time the lid opening data was obtained from sensor module 110. Method 600 may obtain the lid opening data by applying reader device 112, such as an RFID tag reader, to sensor module 110. That is, the actions of this block may be accomplished by pulling lid opening data from sensor module 110 using reader device 112.

At block 604, method 600 obtains expectation data. The expectation data may represent a total number of expected openings of lid 104 over a specified time period, or since a specified event such as a pervious reading of the expectation data. Alternately, or in addition, the expectation data may represent a frequency of openings during a specified time period or since a specified event. Method 600 may obtain the expectation data from storage in an electronic database, which may store expectation data for each of a plurality of compartments outfitted as disclosed herein. The database may be remotely located, but accessible over a network such as the internet.

At block 606, method 600 compares the lid opening data to the expectation data to determine whether the lid opening data represents at least one unauthorized lid opening. That is, based on the expectation data, method 600 determines whether the lid opening data reflects one or more lid openings that are not covered by the expectation data. If so, then the lid opening(s) is/are not authorized, and control passes to block 608. Otherwise, all lid openings are considered to be authorized, control passes to block 610, and method 600 ends.

At block 608, method 600 alerts an operator as to the at least one unauthorized lid opening. The alert may be made in any of a number of ways. According to some embodiments, the operator is alerted by displaying a message on a computer monitor, e.g., a monitor of computing device 114. According to some embodiments, the operator is alerted by sending an email, text message, or phone message. Other techniques for alerting an operator as to the existence of unauthorized lid openings are possible.

Figure 7:
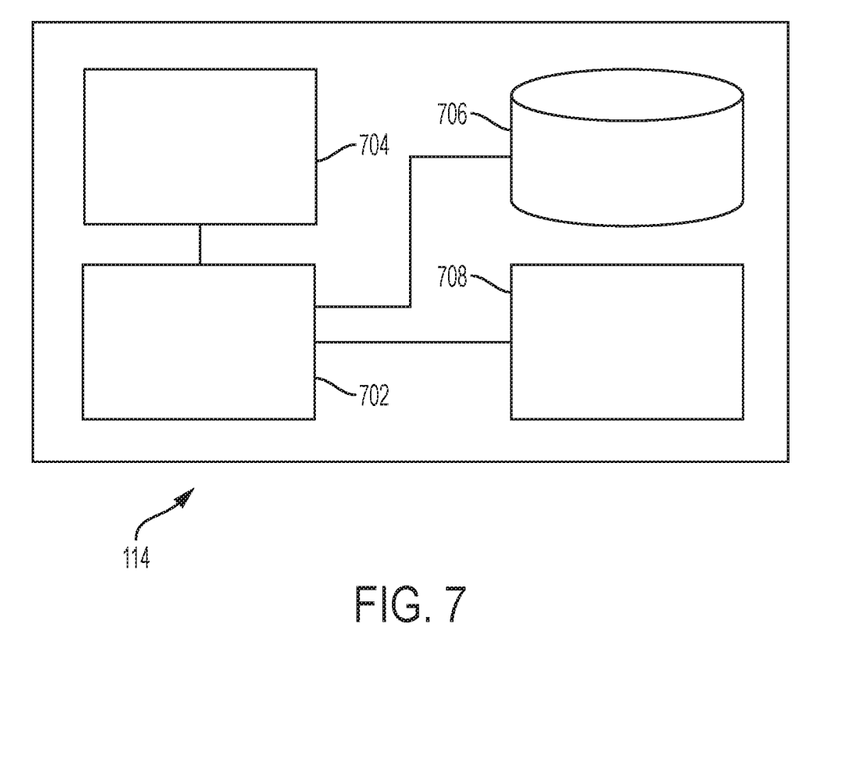
FIG. 7 is a schematic diagram of a computing device according to some embodiments.

FIG. 7 is a schematic diagram of computing device 114 according to some embodiments. Computing device 114 may be based around an electronic hardware computer that include one or more electronic processors 702, which may be communicatively coupled to reader device 112. Computing device 114 may include interface 704 to affect the communicative coupling to reader device 112. Processors 702 may be single- or multi-core processors. One or more processors 702 are communicatively coupled to persistent memory 706, and may execute instructions stored thereon to effectuate at least portions of method 500 and/or method 600. Processors 702 are also communicatively coupled to volatile memory 708. Persistent memory 706 may be in a Redundant Array of Inexpensive Disk drives (RAID) configuration for added reliability, and volatile memory 708 may be or include Error-Correcting Code (ECC) memory hardware devices. Computing device 114 may be communicatively coupled to other computing devices, e.g., by way of a network such as the internet.

Certain examples described above can be performed in part using a computer application or program. The computer program can exist in a variety of forms, both active and inactive. For example, the computer program can exist as one or more software programs, software modules, or both, that can be comprised of program instructions in source code, object code, executable code or other formats, firmware program(s), or hardware description language (HDL) files. Any of the above can be embodied on a computer readable medium, which can include computer readable storage devices and media in compressed or uncompressed form. Exemplary computer readable storage devices and media include conventional computer system RAM (random access memory), ROM (read-only memory), EPROM (erasable, programmable ROM), EEPROM (electrically erasable, programmable ROM), and magnetic or optical disks or tapes.

Those skilled in the art will be able to make various modifications to the described examples without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

What is claimed is:

1. A system for detecting opening of a lid of a compartment constructed of a rigid material, the system comprising:
    a resonator disposed on a wall of the compartment, wherein the resonator has a resonant frequency of mechanical vibration;
    a member disposed on the lid of the compartment and positioned to mechanically perturb the resonator upon opening the lid, whereby opening the lid causes the resonator to mechanically vibrate at the resonant frequency;
    an electronic sensor disposed on the compartment to detect vibrations at the resonant frequency;
    an interface communicatively coupled to the electronic sensor and configured to provide a signal indicating lid opening data representing at least one opening of the lid;
    an electronically stored database comprising expectation data representing expected openings of the lid; and
    at least one electronic processor configured to provide an alert upon determining that the lid opening data is inconsistent with the expectation data.

2. The system of claim 1, wherein the compartment is an aircraft compartment.

3. The system of claim 1, wherein the resonator is positioned on an inside wall of the compartment.

4. The system of claim 1, wherein the sensor is positioned outside of the compartment.

5. The system of claim 1, wherein the interface comprises a radio frequency transmitter configured to send a radio frequency signal indicating an opening of the lid.

6. The system of claim 5, further comprising a base station configured to receive the radio frequency signal.

7. The system of claim 5, wherein the radio frequency transmitter comprises a Radio Frequency Identification (RFID) tag.

8. The system of claim 7, wherein the RFID tag further comprises an electronic memory configured to store an indication of a number of openings of the lid.

9. The system of claim 1,
    wherein the expectation data represents at least one of an expected number of openings of the lid or an intended frequency of openings of the lid.

10. The system of claim 1, wherein the resonant frequency of the resonator is user adjustable.

11. A method of detecting an opening of a lid of a compartment constructed of a rigid material, the method comprising:
    receiving mechanical vibrations at an electronic sensor positioned on a wall of the compartment, wherein a resonator having a resonant frequency of mechanical vibration is positioned on the compartment, and wherein a member disposed on the lid is positioned to mechanically perturb the resonator upon opening the lid, whereby opening the lid causes the resonator to mechanically vibrate at a resonant frequency;
    obtaining an electrical signal from the sensor representing the mechanical vibrations;
    processing the electrical signal to produce lid opening data indicating at least one opening of the lid;
    providing the lid opening data through an interface;
    establishing an electronically stored database comprising expectation data representing expected openings of the lid; and
    providing an alert upon determining that the lid opening data is inconsistent with the expectation data.

12. The method of claim 11, wherein the compartment is an aircraft compartment.

13. The method of claim 11, wherein the resonator is positioned on an inside wall of the compartment.

14. The method of claim 11, wherein the electronic sensor is positioned on an outside wall of the compartment.

15. The method of claim 11, wherein the providing the lid opening data through the interface comprises sending a radio frequency signal.

16. The method of claim 15, further comprising positioning a base station to receive the radio frequency signal.

17. The method of claim 15, wherein the sending the radio frequency signal comprises sending the radio frequency signal in response to an excitation of a Radio Frequency Identification (RFID) tag.

18. The method of claim 17, wherein the radio frequency signal provides an indication of a number of openings of the lid.

19. The method of claim 11, wherein the expectation data represents at least one of an expected number of openings of the lid or an intended frequency of openings of the lid.

20. The method of claim 11, wherein the resonant frequency of the resonator is adjustable.

* * * * *